United States Patent
Hvalsøe et al.

(10) Patent No.: US 11,406,822 B2
(45) Date of Patent: Aug. 9, 2022

(54) SYSTEM FOR ELECTRICAL STIMULATION OF NERVES

(71) Applicant: INNOCON MEDICAL APS, Aalborg (DK)

(72) Inventors: Torsten Fjeldgaard Hvalsøe, Aalborg (DK); Dianna Mærsk Knudsen, Løgstør (DK); Jesper Nielsen, Klarup (DK)

(73) Assignee: INNOCON MEDICAL APS, Aalborg (DK)

( * ) Notice: Subject to any disclaimer, the term of this patent is extended or adjusted under 35 U.S.C. 154(b) by 0 days.

(21) Appl. No.: 15/733,211

(22) PCT Filed: Dec. 18, 2018

(86) PCT No.: PCT/DK2018/050376
§ 371 (c)(1),
(2) Date: Jun. 10, 2020

(87) PCT Pub. No.: WO2019/120420
PCT Pub. Date: Jun. 27, 2019

(65) Prior Publication Data
US 2021/0101006 A1    Apr. 8, 2021

(30) Foreign Application Priority Data
Dec. 18, 2017   (DK) ............... PA 2017 00724

(51) Int. Cl.
*A61N 1/36* (2006.01)
*A61N 1/04* (2006.01)
*H01B 5/16* (2006.01)

(52) U.S. Cl.
CPC ....... *A61N 1/36007* (2013.01); *A61N 1/0456* (2013.01); *A61N 1/0496* (2013.01); *H01B 5/16* (2013.01)

(58) Field of Classification Search
None
See application file for complete search history.

(56) References Cited

U.S. PATENT DOCUMENTS

| 4,196,737 A | 4/1980 | Beilacqua |
| 4,362,165 A * | 12/1982 | Carmon ............ A61B 5/25 600/396 |
| 6,845,272 B1 * | 1/2005 | Thomsen ............ A61N 1/046 607/153 |

(Continued)

FOREIGN PATENT DOCUMENTS

| DE | 102010046920 A1 | 4/2011 |
| EP | 2314345 A1 | 4/2011 |

OTHER PUBLICATIONS

International Search Report for International Application No. PCT/DK2018/050376, dated May 31, 2019, 3 pages.

*Primary Examiner* — Michael W Kahelin
(74) *Attorney, Agent, or Firm* — Holland & Hart LLP

(57) ABSTRACT

Neuromodulation electrodes and related methods to treat pelvic floor disorders, such as urinary and/or faecal incontinence, using electrical stimulation of the left and/or right branches of the dorsal genital nerves, or pudendal nerve, using a highly flexible electrode unit to obtain stable and comfortable contact with the cutaneous tissue or mucous membrane at or near the glans of the clitoris, in close proximity of the targeted nerve, for stabile neuromodulation applications.

19 Claims, 3 Drawing Sheets

(56) References Cited

U.S. PATENT DOCUMENTS

| | | | |
|---|---|---|---|
| 2006/0095001 A1 | 5/2006 | Matsumura | |
| 2007/0173916 A1 | 7/2007 | Axelgaard | |
| 2009/0062897 A1* | 3/2009 | Axelgaard | A61N 1/0452 607/152 |
| 2014/0073896 A1* | 3/2014 | Hyatt | A61N 1/048 600/391 |
| 2015/0290451 A1* | 10/2015 | Bouton | A61N 1/0452 607/48 |
| 2017/0182320 A1* | 6/2017 | Kolb | A61N 1/36014 |

* cited by examiner

SYSTEM FOR ELECTRICAL STIMULATION OF NERVES

CROSS REFERENCE TO RELATED APPLICATIONS

This application is a U.S. National Entry and claims priority to PCT International Patent Application No. PCT/DK2018/050376, filed 18 Dec. 2018, and entitled "SYSTEM FOR ELECTRICAL STIMULATION OF NERVES", which claims priority to Denmark Patent Application No. PA 2010-0724 filed 18 Dec. 2017, the entire disclosures of which are incorporated herein by this reference.

TECHNICAL FIELD

The present invention is generally concerned with electrical stimulation of nerves. More specifically, the invention relates to neuromodulation therapy including treatment of pelvic floor disorders, such as urinary or faecal voiding dysfunction. The neuromodulation treatment utilizes electrodes combined with use of a pulse generator containing predetermined programs adjustable by caretakers and/or users.

BACKGROUND OF THE INVENTION

Medical research has shown beneficial effects of electrical stimulation of the dorsal genital nerves for the treatment of urinary and faecal incontinence. The dorsal genital nerves are composed of purely afferent/sensory fibres and unwanted motor functions activated by electrical stimulation of these are thus not present.

Incontinence disorders may afflict people of all ages, genders and races, and may be associated with illness, injury, and/or aging. Electrical neuromodulation has shown to be effective in eliminating or drastically reducing the severity of symptoms of such dysfunction, such as urinary or faecal incontinence.

The dorsal genital nerves are superficial on the dorsal side at approximately the upper ¼ of the cross section of the penis and runs the in the length of the shaft of the penis until it reaches the glans, where it fans out.

In females the dorsal genital nerves tend to be close to the mucous membrane (or skin) near the glans of the clitoris between the labium minus and labium majus.

Thus, these sites of stimulation are effective for both males and females, since factors such as absence of fat layer and muscle tissue have a significant positively influence on the activation of the targeted nerves. At the intended site of stimulation, the fat layer is limited, and no muscles cover the nerves [DOI:10.2298/JAC0802035K Electrodes for transcutaneous (surface) electrical Stimulation, 2008.].

The nerves to be targeted for the specific product are the dorsal genital nerves (clitoris/penile nerves), which are possible to access with surface electrodes using suitable stimulation settings [H. B. Goldman et al, Dorsal genital nerve stimulation for the treatment of overactive bladder symptoms, Neurourology and urodynamics, vol. 27, no. 6. pp. 499-503, January 2008; J. Worsøe, L. Fynne, S. Laurberg, K. Krogh, and N. J. M. Rijkhoff, The acute effect of dorsal genital nerve stimulation on rectal wall properties in patients with idiopathic faecal incontinence, Colorectal disease: the official journal of the Association of Coloproctology of Great Britain and Ireland, vol. 13, no. 9, pp. e284-92, September 2011; Fjordback et al, Event driven electrical stimulation of the DPN for management of Neurogenic Detrusor Overactivity in Multiple Sclerosis, Neurourology and Urodynamics 25:349-355 (2006)].

However, these sites are also very challenging for conventional surface electrodes, due to large tissue movements during daily activities, and complex tissue geometry of which they may have to be attached. For applications, where continuous stimulation is crucial for the successfulness of the treatment provided, daily activity further challenges present available surface electrodes to remain functional in the intended position.

Surface or patch electrodes have been used for electrical stimulation of nervous tissue for decades. Current available transdermal patch-electrodes are therefore to be considered as a standard conventional means for surface stimulation and are frequently used for various applications targeted almost all over the human body, also including veterinary applications. The target area is the genital region i.e. near the pubic symphysis and/or in close proximity of the clitoris or prepuce hereof. They shall be allowed to be applied to hairy skin, especially considered important for female use. Shaving is known to create skin irritation and itching in many cases and may thus be uncomfortable for many users. The anode or return electrode may be positioned in close proximity of the cathode electrode or stimulating electrode, or distant. The latter may provide an option for a relative larger electrode, thus eliminating many of the fixation issues to be addressed for the cathode electrode.

Patch electrodes are fixed to the skin typically by use of an electro-conductive tacky gel surface, or alternatively by use of acrylic or rubber based adhesive supports. An electrode of this type is disclosed in U.S. Pat. No. 4,066,078 to Berg. Most often such electrodes are used for scheduled events or sessions treatments (out-patient therapy sessions) and require the user to have limited movement due to risks of loosening, and hence consequently loss of effect. Other electrodes can be worn for days, e.g. in applications such as event and Holter monitors, or for use as means for patient screening procedures.

Effective neuromodulation of the dorsal genital nerves relies on good contact to the targeted tissue. Good clinical effect relies on constant electrical performance between the stimulating electrode and targeted tissue. Thus, the overall target is to design electrodes that include features, which will prevent these from moving, falling off, or in any other way loose contact to the targeted tissue during daily use. Further, the electrode designs shall allow convenient doffing. Due to the hygienically aspect, the electrode concept shall also address the needs for hygienically acceptable solutions for both males and females. For this reason, disposable electrodes are preferred, but electrodes with limited use cycles are acceptable, and hence high mechanically integrity is not of real concern.

An adhesive patch is often conveniently cut to individual shapes, to meet certain needs. However, most patch electrodes designs make only poor attempts to fit to anatomical challenges of the targeted structures, and thus are mostly varied in sizes to avoid sensations, skin burns and reduce hot spots, tailored with the charge to be injected.

For situations where physical activity is unavoidable, conventional patch electrodes require some sort of additional support to remain fixated and functional in the intended position. Such supports are normally used to improve the electrode fixation, includes various means such as of tapes or for brain sensing electrodes, the helmet array fixture is well-known, and are thus not an enhancement of the adhesion effect of the actually active stimulating surface, which is one of the main purposes of this invention.

The application of the product of this invention may require either quick-onset of the stimulation if/when requested or continuous use during day and/or night, depending of the clinically supported setup for the specific patient/user. Thus, the reliability of the electrode to remain in position and being functional is of higher importance for this product and may be a different use scenario compared to many other applications currently on the market. The important aspect of freedom of movement required during everyday activities such as walking, biking, running or other sports activities is even further stressing out the importance of reliable and comfortable electrode fixation. The requirement for quick onset, challenges the interfacing electrode in such a manner that it is not possible to correct or re-position the electrode in a timely manner.

Appropriate contour design is advantageous but is not considered crucially important. Well-designed charge-limits for minimal active areas are required to avoid unacceptable risks of skin/tissue burns. Also, edge biting/stinging should be appropriately addressed. Supportive elements should not create overdue burden of donning/doffing and should not result in unacceptable pain and skin irritation as a result of use, including removal. If these challenges are unmet, the electrode will not be suitable for long term use.

The U.S. patent application US2015/0352357 by Medtronic represents one method of electrode fixation where the stimulation system is relying on good tissue contact by means of briefs/panties/underwear. For male users, additionally an electrode formed as a flexible ring is offered for support. However, none of these designs specifies or present any suitable means that meet the previously described challenges of electrode fixation. Especially solutions for female users are requested. The principle provided for the male electrode ring support is an often-used method in many applications.

Conventional surface or patch electrodes have the lead strands placed onto a scrim or mesh, distributing the current evenly to the gel-member. Swaged type snap connectors are typically positioned in a rigid polymer sheet, interfacing directly to the underlying gel-member, typically supported by another rigid polymer-based sheet layer. These components unfortunately also constitute elements adding stiffness to the final electrode that hinder prior art electrodes to stay in functional contact with the tissue near the female dorsal genital nerves.

Of the electrodes presently available, the processing methods share many similarities with pressure sensitive adhesive tape manufacturing, utilizing conversion techniques including die cutting to form the electrode patch. In addition to these methods, adhesively based assembly techniques are used for lead attachment, or stamping a swaged connector or magnets into the patch part of the electrode. Many electrodes offer combination structures including a metallic or otherwise conductive support member to which an electrical lead from an associated pulse generator may be attached. The gel-member of prior art electrodes is extruded into a layer or sheet. Layers with various properties may constitute a final gel-member as described in EP1052933B1 to Axelgaard.

The prior art electrodes most often describe a design where continuous scrim fabrics, polymer-sheets and metallic meshes are implemented, and supports the flexible gel-element. Therefore, the aim of those inventions is to provide suitable means for positioning and holding in place the gel-member of a transcutaneous electrical stimulation electrode, while the focus on the required softness and flexibility of the electrode unit necessary for the application onto complex geometry tissue, such as the female prepuce and labia minora is not considered. The final electrode unit should resemble the tissue onto which it is applied. None of the currently available prior art electrodes exhibits the level of flexibility required to remain functional in the intended position of stimulation.

Because of the poor strength and high notch sensitivity of the electro-conductive gels, a scrim layer is often embedded onto the gel-member in order to enable handling of the gel-member component and its application to a surface of a conductive member. This limits the flexibility of the prior art electrode designs. In conventional surface electrode designs, the rear side of the electrode unit often consists of a fabric, typically made from spun-bonded polyolefin fibres. This scrim layer may also be positioned elsewhere in the laminated structure of the electrode. The non-flexible spun-bonded fabric scrim layer fixates the lead component to the electrode assembly and constitutes the main structural element of the final electrode.

Thus, there is an urgent need for providing a reliable means of electrode fixation onto the skin having anatomical structures and complex tissue geometry.

SUMMARY

It is an object of the embodiments of the present invention to provide a system, which overcomes or at least reduces the above-mentioned disadvantages.

Referring to the above explained advantages of a scrim layer and the effect of omitting a scrim layer, the gel-member may stretch or distort during handling, but it has to be understood that for this invention, this is a desired effect, and features of the gel-member reduces internal stresses in the gel-member to a minimum.

The electrode unit of this invention, hereby also defined as the "electrode" presents an unmatched flexibility, and constitutes a design specially adapted for applications onto tissue with complex geometry, such as the female prepuce to target the dorsal genital nerves.

The disclosure is directed to stimulating electrode fixation onto anatomical challenging structures with geometrically complex curvatures, having designed features that allow the electrode unit to adapt to the surrounding tissue onto which it is applied. The design includes a forming shell-member that constitutes a physical and structural frame for the conductive gel-member of the electrode, which is specifically formulated to be soft and flexible, while still being retractable from the skin. This is solvable due to the properties of the shell-member wall or included details of a matrix-member being part of or added to the shell-member. The combined structures and elements constitute active stimulating electrode unit designs of various shapes and sizes, when applied with either type of connector. The structural shell-member is designed to adapt to the naturally curvatures of the skin, with the purpose of delivering of transcutaneous electrical stimulation, and shall therefore constitute a flexible element.

The shell-type gel-fixation member shall allow application of a soft gel component onto the anatomic structures of the female genital perineum and the male genitals near the pubic sympysis, while hindering adhesion to any garment used. The flexibility of the complete electrode unit should ideally closely mimic that of the tissue onto which it is applied. Although softer and more flexible assemblies is not constituting a functional concern, it may consequently limit the lifetime of the electrode unit, or even hinder reuse of the electrode unit.

In a first aspect of the invention, is provided an electrode specially adapted for providing suitable electrical contact and fixation to the patient's skin in regions with irregular tissue structures, the electrode unit comprising a flexible nonconductive shell-member forming a body structure, a flexible matrix-member, a conductive member, a connective member including means for connection to an external pulse generator, a rubbery gel member, where the flexible matrix-member is arranged in the shell-member and fixates the conductive member and supports the rubbery gel-member, the conductive-member forming a means for evenly distributing electrical connection from the connective member to the gel-member and where the rubbery gel-member is further providing mechanical fixation of the electrode unit to the patient's skin.

In a further embodiment a second conductive gel-member is arranged between the shell-member and the rubbery gel-member. This has the effect of enhancing the flexibility of the electrode unit.

More specifically explained, an electrode in accordance with the present invention, suitable for stimulation of the dorsal genital nerves, generally includes a shell-member acting as a substrate for a conductive member, including means for providing electrical connection to a pulse generator. In addition, the electrode includes a matrix-member, onto which a conductive member, be any suitable type of graphene or graphitized coating, silver-based coating, or a conductive sponge or conductive fabric mesh member, is positioned or applied. The above described element is filled with an electrically conductive gel-member and a rubbery gel-member as means for providing the electrical interface to a patient's skin, the gel-member being adhered to the conductive member added onto the matrix-member.

In an embodiment, the matrix-member is furnished with a conductive member being one or more of a graphene or graphitized coating, silver-based coating, or a conductive sponge or conductive fabric mesh member In an embodiment, the shell-member comprises natural- or artificial-rubber of a durometer less than or equal to A shore 50.

In an embodiment, the natural rubber is latex.

In an embodiment, the artificial rubber is one or more of silicone, thermoplastic elastomer (TPE) or thermoplastic urethane (TPU).

In an embodiment of the electrode unit the shell-member, wherein the matrix-member is arranged and is constituting a physical means of enforcing the rubbery gel-member and holding the rubbery gel-member into its intended position, while providing means for the connecting member to form electrical contact to the conductive member, the shell-member forms a protective element towards the clothing or other parts of the body not intended to be stimulated. In this manner, the matrix-member functions as a chassis-like component.

In an embodiment, the matrix-member comprises a number of protrusions and/or cavities the protrusions forming pins and the cavities forming dimples, the pins and/or dimples having a first end and a second end, the first end interfacing the shell-member and the second end interfacing the rubbery gel-member.

In an embodiment, the pins and/or dimples are distributed over the footage of the shell-member and protrudes out from or are formed into the shell-member in a straight or angled direction.

In an embodiment, the pins and/or dimples are an integral part of the shell-member.

In an embodiment, a low friction coating is provided to at least a part of the shell-member outer surface.

In an embodiment, the electrode unit includes a uniform gel-member arranged and cured within the shell-member and matrix-member substituting the rubbery gel-member and the second conductive gel-member in one component to constitute the means for contact for both to the conductive member and to the patient's skin.

More particularly, the matrix member constitutes an element which limits the need for high peel strength of the applied amount of conductive gel-member to form contact to the conductive member. Thus, a uniform rubbery gel-member constitutes a means for contact for both to the conductive member and to the patient's skin.

However, to increase the flexibility and softness of the gel-member, a first volume of a low or non-plasticized (commercially available as e.g. AmGel® AG2500 series, or AG700 series) conductive gel compound is arranged into the shell-member forming contact to the matrix-member, which is then covered with another more rigidly plasticized (commercially available as e.g. AmGel® AG500 series) conductive gel compound to form the interface to the patient's skin or vice versa. To tailor the differing characteristics of the first and second volume of the gel-member, the first volume comprises none or less glycerol or similar plasticization agent, than the second volume.

In an embodiment, the electrode unit, includes a first volume of a gel-member which is thixotropic non-plasticized with high viscosity and a second volume of the gel-member is plasticized to form a rubbery structure, where these are forming an electrically conductive gel-member providing electrical connection to the patient's skin.

In an embodiment, the connective-member is having multiple conductive strands.

In yet another embodiment, the multiple connective strands are distributed in a fan shaped manner and positioned within the matrix-member or internally in the shell-member above the matrix-member.

More explicitly, to further aid a uniformly current distribution over the interface to the patient's skin, the lead wires having multiple strands being untangled in the end are distributed within the matrix-member in a fan shaped manner, prior to the addition of the conductive member. This additionally has the effect that the stiffness of the lead wires is evenly distributed to form a uniform and very low flexural stiffness element. Thus, a stiffness element concentrated along the lead wires is avoided. The often observed result of poor and/or unreliable current densities provided by larger prior art electrodes is thus accommodated by means of the gel supporting matrix-member positioned in the shell-member, which provides mechanical structure for the electrode unit, without compromising the softness or flexibility of the electrode unit.

Since the elements of the electrode unit of this invention are all applied with the aim to decrease the overall stiffness of the electrode unit in any direction, a fixation structure for the lead wire or the swaged snap connector, or magnet connection is required for necessary mechanical strength, forming a strain relief for the connector member strands. This is solved by arranging a component of limited extent, to where the lead wire penetrates the wall of the shell-member to form electrical contact to the conductive member positioned on the matrix-member. This is preferable an integrated moulded section of a high durometer silicone, as this has the least impact on the overall stiffness of the electrode unit. However, a cut to size scrim adhered to the outer side of the electrode unit prior to application of the low friction coating is another suitable solution.

More specifically, in an embodiment of the electrode unit it comprises a non-conductive shell-member including means of a structural support for the connector member, in the form of moulded details forming a cavity or a partially covering scrim layer of limited extent.

In an embodiment, where a first volume of the gel-member is non-plasticized, a thickener being one or more of ethylene copolymer or gelatin is added.

In a further embodiment, the matrix-member is configured with a density of the matrix-member, which matches the viscosity of the first volume of the gel-member, so that these two elements secure electrical contact to the conductive member, and the first volume of the gel-member stay interlocked in the matrix-member. In this way, the matrix-member constitutes a soft elastic and flexible structure.

In one embodiment, the wall side of the shell-member are designed with overly length of edge line.

In a further embodiment the edge line is forming a curtain like meandering shape adding an expansion spring feature to that edge line.

To increase flexibility of the wall lips, these can be designed having a curtain like design, reducing or eliminating the need for a highly flexible material. Wall heights of up to 10 mm are feasible.

In an embodiment, the wall side height is less than or equal to 10 mm.

The gross design of the shell-member is for the preferred solution a droplet shaped to provide options for the user for individual positioning. However, the shape may be rectangular, square, circular, and oval or any other shape, as the shape is not crucially important for the overall functionality of the electrode design but should be adapted for the therapy and anatomic area it is applied to. Thus, in an embodiment, the shape of the shell-member is one of a droplet, rectangular, square, circular or oval or multisided.

This design increases the flexibility of the electrode unit, minimizing stresses in the edge line of the electrode unit, and provides additional grip for the gel-member the gel-member further being fixated in the shell-member In a further embodiment, the electrode unit further comprises a flexible matrix-member being one of a conductive open cell sponge, a conductive fabric, or conductively coated moulded structures of tailored density is forming adhesion support for the second rubbery gel-member.

In an embodiment where the matrix-design constitute a specific density of pins and/or dimples, the surface area and quality of that matrix-member is configured to the viscosity and/or adhesion properties of the gel-member. The pin and/or dimple design in that matrix-member shall constitute sufficient area, while additionally enhancing the integrity of the gel-member. It is important that the pin design is notch resistant. In an embodiment the matrix-member has an elongation before break that is at least similarly to that of the gel-member or at least an elongation before break of 100% strain. The pin and/or dimple design should preferably have a length to diameter ratio of more than 2:1, otherwise additional dimples or cavities may be required. This means that for many applications the pin length or dimple depth become longer than 2 mm. However, the length of the pins and depths of the dimples should be designed with respect to the overall footage of the part that is intended to interface the skin. Thus, a smaller footage could introduce pin lengths and dimple depths shorter than 2 mm without jeopardizing internal structure strength and integrity of the electrode unit. It is foreseen that pin lengths in such applications could be as short as 0.1 mm and still be providing a sufficient grip integrally in the electrode unit. However, pin length and/or dimple holes could be as high or deep as 10 mm. Thus, in an embodiment a pin length and/or a dimple depth of at least one pin or dimple is in the range 0.1 mm to 10 mm.

Under-cutting holes provide additional grip and can completely or partly replace the pin-elements but requiring a certain wall thickness of the shell-member. The elongated pins which in an embodiment are forming the matrix member protrudes out from the shell-member. The orientation can be in straight angles facilitating the interface to better receiving the conductive member. In an embodiment, at least parts of the elongated pins are protruding out from the shell-member in an angled direction. This facilitates a better grip to the gel-member and rubbery-member and provides a better resistance towards disintegration of the electrode unit. The pins do likewise the dimples, being under-cut, not have to be regular in shape. It is thus within the scope of the invention that in an embodiment, the pins and/or dimples over the travel length, has a varying diameter and/or cross section.

Further length or larger ratio constitutes an advantage of both integrity protection of the gel-member but also for providing additional adhesion to the shell-member rather than to the skin of the patient. However, other length to diameter ratios is acceptable when the lip design in the shell-member is proper supporting the grip feature of the matrix member. Additionally, the length of the pins in this matrix-member design is also influenced by the density, by the meaning of the number of pins per square unit. Therefore, in high density matrix-designs lower pin designs are also acceptable, when correctly tailored with the gel-member applied. The density of the matrix need not be constant but can in some designs advantageously be with a higher density at the edge line than at the center, since the edge line is experiencing higher strain when removing the electrode unit form the skin. The curtain edge line design also adds to the grip effect to the gel-member, by adding the surface are in contact of the shell-member to the gel-member.

The matrix-member additionally constitutes a means of enhancing the integration of the conductor wire strands to the conductive member, and also to the shell-member. The matrix member design additionally enhances the area and/or volume of the conductive member, further lowering risks of charge density hot spots.

The matrix-member can be considered as a chassis member, which integrates the elements constituting the electrode unit. In one embodiment the matrix-member is an integral part of the shell-member. In an embodiment, the matrix-member is added to the shell-member, by means of a conductive open cell sponge, a fabric, scrim or mesh.

It has to be understood, that the matrix-member must not constitute a stiffening element, and thus the matrix-member shall constitute flexible materials, and/or highly open structures, i.e. steel-wool. In an embodiment, the matrix-member includes a steel wool. For the sake of completion, it is appreciated that the term steel wool is not only covering wool made of steel but in its broader meaning where steel wool also can be made of different qualities of iron, low-grade carbon steel wire, aluminum, bronze or stainless steel. The metal is shaved into thin strands that, when bunched up in a fuzzy mass, resemble wool. Hence, the features of the matrix-member and the properties of the gel-member shall be matched for this embodiment.

In an embodiment, the strands of the lead connector are distributed in a fan like shape on the inside of the shell-member, prior being coated with a conductive carbon/ graphene-based material. In an embodiment, the electrode-unit further includes a snap or a magnetic attractable connector or a magnetized connector arranged with the shell-member. A snap or magnetic connector can, even though it represents a stiff element, in thicker designs be mounted into or onto the shell-member. The underneath surface shall however then have a surface finish that allow sufficient adhesion to the gel-member applied. The patient may in designs utilizing snap or magnetic connector, connect the product to the electrode unit, before applying the electrode onto the intended stimulation site. The snap or magnetic connector also constitute means of an applicator to position the electrode as intended.

The outer side of the electrode unit, i.e. the side pointing away from the target tissue, shall have a low friction surface property to not stick to the underwear of the patients choice. In the preferred design, this is obtained by spraying the outer silicone surface with a low friction silicone based addition curing coating, such as commercially available NuSil MED 6670 or a proper selected parylene based coating.

The cross-sectional profile determines some of the flexibility properties, although the combination of gel-fixation, shell-member shape, dimensions and materials and the gel component all play a role for the flexibility of the final stimulation electrode unit.

The lens or droplet shaped electrode unit may feature a gel component following the internal shape, to also constitute a lens shape, i.e. have a pre-shaped form and thus to follow specific tissue intended for stimulation. This is obtained by a process of filling the shell-member and let the gel-member to cure subsequently.

A typical patch lead design as connective member is superior for its flexible nature. However, since the electrode itself is designed to be highly flexible, a typical swaged snap connector or a magnetic connector could be used as well, especially optional for thicker electrode designs. Other connection elements such as a magnet can be applied, especially if the magnetic connector is designed with a main longitudinal shape at the main bending line of the electrode.

The gel material typically used for patch electrodes for transcutaneous applications, such as low modulus rubbery gel formulations can also be used in combination with the shell-member. The gel compound material properties can however be tailored to meet the overall flexibility level of the final electrode unit design.

In an embodiment, the electrode comprises a gel-member configured to be highly thixotropic and with a relative high viscosity and a shell-member being molded of soft silicone having a matrix-member with matched density.

Designing a gel compound material with a relatively high viscosity and arranging it in combination with a soft silicone molded shell-member with matched matrix-member density, results in the highly flexible electrode unit design.

In an embodiment an electrode unit includes a gel-member constituting multiple gel elements, thus increasing the flexibility of the final gel-member itself. A series of combinations of fluid gel materials and rubbery gels plasticized with various durometer levels forms the final gel-member. By careful combining the viscosities of the gel elements, the final gel-member can be made further flexible. A firm rubbery gel element is used at the edges of the electrode unit, whereas the center-positioned gel element is almost liquid in its behavior. A liquid-like gel is positioned in the bottom of the shell-member, with a cap of rubbery gel that constitutes the electrode/skin interface.

In an embodiment an electrode unit includes a prefabricated shell-member of low durometer coated with a conductive member configured to evenly distribute the electrical charge in the electrode unit and providing electrical connection to a connective member arranged with the a flexible matrix-member, said matrix-member providing fixation of a first liquid-like gel-element filled into the matrix member, to a level where the matrix-member provides mechanical support for a second rubbery gel-element converted from a sheet of pre-cured hydrogel, which forms a barrier of the liquid gel-element and forming contact to the patients skin.

Even though the invention is explained using a specific embodiment that targets a system for the treatment of urinary incontinence, it will be appreciated that the application is not limited by this application but covers all applications of surface stimulation intended for neuromodulation, where the invention solves the technical problem of providing a device with technical features that facilitate electrical stimulation using electrodes that shall stay in the intended position.

BRIEF DESCRIPTION OF THE DRAWINGS

For the purpose of illustrating the invention, forms are shown in accompanying drawing, which are presently preferred, it being understood that the invention is not intended to be limited to the precise arrangements and instrumentalities shown.

DETAILED DESCRIPTION

For the purpose of illustrating the invention, forms are shown in accompanying drawings, which are presently preferred, it being understood that the invention is not intended to be limited to the precise arrangements shown.

Figure 1:
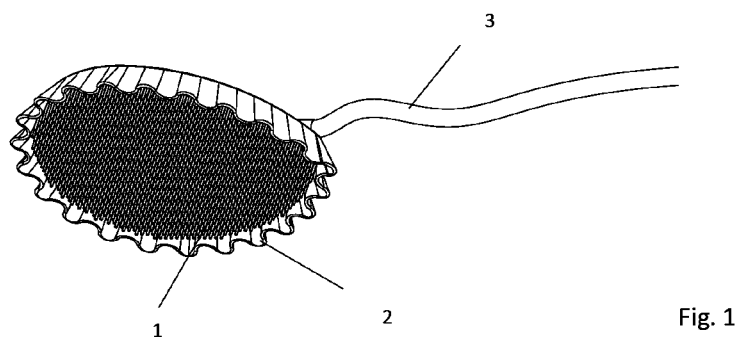
FIG. 1 illustrates the electrode unit side to be applied onto the skin of the patient. It comprises one version of the matrix-member details, the lip design for enhancing the flexibility of the shell-member, and a lead providing the stimulating signal to the electrode. The electrode unit consists of a matrix-member having details shown as the pin design (1), the boundary lip design providing a geometrically flexible edge for the electrode unit (2), and which have a conductible graphitized coating constituting the conductive member which distributes the electrical energy uniformly to the skin. The signal is provided by a pulse generator through the lead (3), the pulse generator not included in the drawings.
Figure 8:
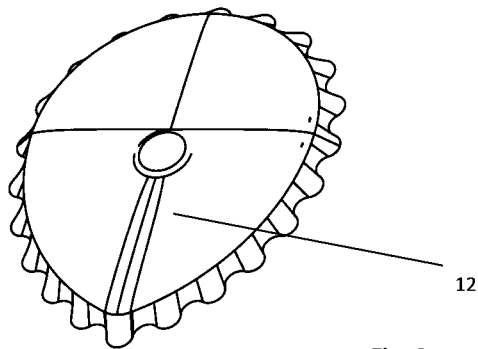
FIG. 8 illustrates the externals of the embodiment described in FIG. 7, with the magnetic connector element (12) positioned centrally in the shell-member.

FIG. 1 is representing one embodiment of the electrode unit utilizing a classical lead connection (3). A typically used snap connector is another means for connecting a lead to the pulse generator, shown in FIG. 6, and further magnetic connector is shown in FIG. 8. Other electrically connectors are optional, such as jack-connectors or any other type, suitable for means of connection to a pulse generator.

The geometrical surface area of the electrode unit is at least 25 mm2 to prevent too large charge densities eventually irritating the tissue. The shape of the surface electrode unit of FIG. 1 is designed to aid various positioning options of preference of the user. The shell-member of the electrode unit can be made from various polymers such as e.g. low durometer silicones, natural or artificial rubber, latex, injection molding thermoplastic elastomers or rubbers or even urethanes. It has to be appreciated that the materials applied shall form a highly flexible shell-member, thus other materials that has similar properties should also be considered optional means, and within the scope of protection of the invention.

Figure 6:
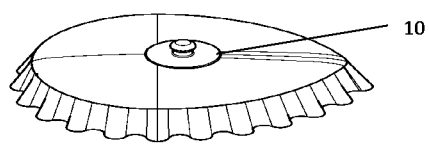
FIG. 6 illustrates the electrode unit in an embodiment featuring a swaged type snap connector (10)
Figure 7:
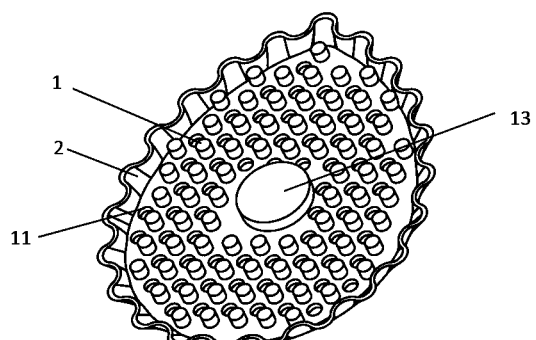
FIG. 7 illustrates the electrode unit side to be applied onto the skin of the patient. It comprises a further version of the matrix-member details (1) positioned in the shell-member, the lip design for enhancing the flexibility of the shell-member and provide additional gel-member fixation, and a magnetic-based contact element (13). The electrode unit consists of a matrix-member having details shown as a combined pin and dimple/cavity design (1 and 11), and the boundary lip design providing a geometrically flexible edge for the electrode unit (2)

The lead part of the attached leaded connection, or the connected lead shall preferably be soft and pliable, and for embodiments utilizing a swaged snap connector or magnetic connector as presented in FIG. 6 and FIG. 7 respectively, the thickness of the electrode unit shall be large enough to allow the stiff parts of the connector element to move or tilt, relative to the skin onto which the electrode unit is fixed. In the preferred design, where the shell-member is made from flexible silicone, the section of the material into which the snap connector is fixed, is made from a more rigid type silicone, to enhance strength of the assembly. A ring element of the size of the snap connector is thus made from a high durometer silicone, which is molded into the shell-member. Another way to establish suitable mechanical connection is by means of gluing the snap og magnetic connector into the shell-member, by either converted tapes or fluid glues.

Figure 5:
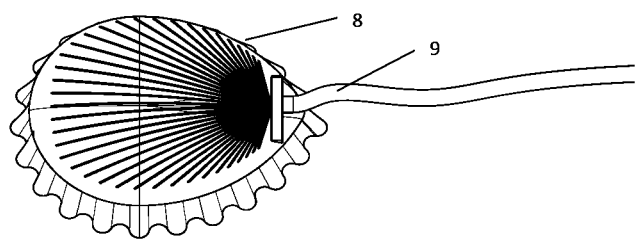
FIG. 5 illustrates the fan shaped lead wire strand distribution (8), which disperse the wire strands internally in the matrix-member, positioned inside the shell-member of the electrode unit. Additionally, a lead connector fixation element (9) is shown as molded on top of the shell-member of the electrode unit.

For embodiments utilizing a leaded type connection, the conductor part of the lead shall penetrate the shell-member to reach into the gel-member, establishing the electrical connection to the skin/tissue of the patient. A part of the lead shall be fixed to the outside of the shell-member as illustrated in FIG. 5, where a bridge-element is fixating the lead to the outer side of the shell-member.

The major part of the electrode design is the shell-member, into which the gel-material is arranged, and the connection member providing the stimulating signal. While the gel-member shall provide adhesion to the skin to be electrically stimulated, the outer surfaces of the shell-member shall be non-tacky and not adhesive. This is reached through application of a low friction top coating-member, and/or having a smooth surface structure to limit tack to any garments or other parts of the body, which provides a means for reducing the risk of unintentionally pushing off the electrode.

The major properties of the shell-member is however, that although it is highly flexible, it has a physical structure when moulded, and thus supporting the gel-member of poor mechanical strength. The ultimate elongation before break of the shell-member shall be at least 25%, given the requirements of flexibility. However, the stress-strain properties of the shell-member should be comparable to that of the applied gel-member, and thus the strain at break should preferably at least 100%. Above this level, a further advantage is present, although with only limited improvements of the properties of the overall electrode unit.

Figure 2:
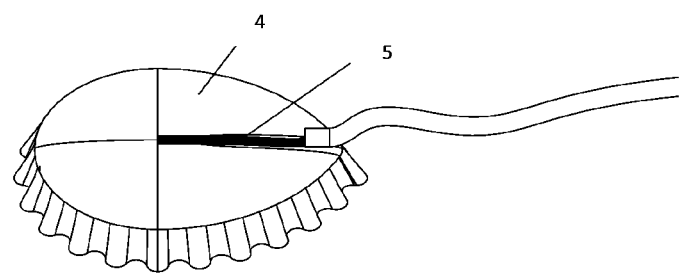
FIG. 2 illustrates the electrode unit from the top face, pointing away from the patient. It comprises a low friction top coating-member, having a smooth surface structure to limit tack to any garments (4), and the lead type connector distributing interface for the stimulating signal (5) provided by the pulse generator.
Figure 3:
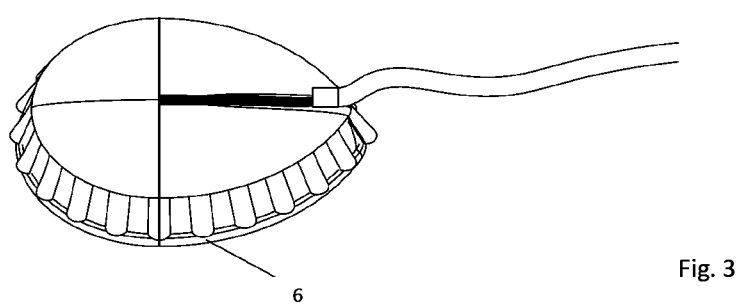
FIG. 3 illustrates the electrode unit with the gel-member (6) positioned inside in the shell-member, in an embodiment utilizing overfilling of the shell-member, creating a highly tacky lip design, extended below the shell-member lip design (2)

In FIG. 3, the overfilling of the shell-member is illustrated as an additional lip positioned below the curtain edge details. The overfilling could also be established by filling the shell member to the edge line of the curtain design, as illustrated in FIG. 2, and further on top of this, a sheet of pre-cured gel is positioned as a lid. In this manner, more aqueous gel-compounds can be included as part of the gel-member.

Figure 4:
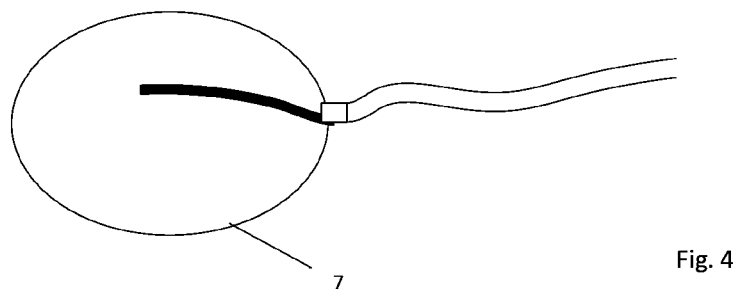
FIG. 4 illustrates the electrode unit from the top face, pointing away from the patient. In this embodiment, the shell-member design is shaped as a lens (7). The lens utilizes no internal gel-fixation matrix-member, and thus shall be combined with a gel-member of appropriate plasticization and tackiness. A second gel-member for increased skin adhesion may be applied.

In thinner designs, or lens shaped designs as illustrated in FIG. 4, means of special surface treatments which manipulates the physical or morphological properties of the shell-member inner surface in such a way and to such a degree that acceptable levels of adhesion to the gel-member is established, and thereby these means are constituting the matrix-member. The treatment shall be balanced with the properties of the gel-member which shall be designed to be sufficiently rubbery in its character. It is however key performance criteria that the assembled electrode remains sufficiently flexible in any direction, and thus the gel-member cannot be too rigid.

In FIG. 5, a fan-shaped distribution of the conductive parts of the lead connector-member is presented. This method of conductor distribution provides a means of equally charge distribution into the gel-member, and thus further providing equal charge distribution all over the active electrode area. Additionally, the fan-shaped conductor distribution adds stability to the gel-member and functions as a matrix element, or an enhancement of the matrix-member. If the conductive parts of the lead are of further length, these can be crumpled into a mesh element constituting a matrix-member. However, this will not result in an as nicely charge distribution, although it may be suitable for smaller electrode applications.

The fan-shape is established by having an equally distributed number of strands of the conductive lead spread over the matrix-member, and then the conductive strands are then manipulated into the matrix-member. The gel-member is the poured over the matrix-member, soaking the conductive parts of the lead, and subsequently cured. In this manner, a flexible solid component constituting the electrode is formed.

Graphitized coating materials or any other typically used electrically conductive material e.g. silver based coatings can be used alone, or added, to improve the distribution of the stimulation current evenly over the gel face or acting as a conductive member on its own. To further aid the current to become evenly distributed all over the electrode/skin interface, the connector-member part having interface to the conductive member in contact with the gel, shall be designed to have proper electrical properties. In embodiments utilizing the magnetically enhanced connection, as illustrated in FIG. 7, the properties of the gel shall compensate for the less optimal current distribution directly below the magnet-element. Otherwise the magnet element shall either not be part of the electrical connection, or it shall be electrically isolated directly the magnet itself, to not form a hot spot, concentrating the current distribution.

Figure 9:
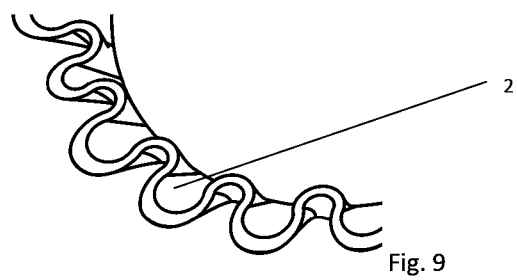
FIG. 9 illustrates a detailed view of the curtain edge design (2), which can be part of any of the previous described figures. The curtain-edge, having a plurality of at least three curvatures forming an irregular or regular overly long edge line, is providing additional flexibility and further fixation of the gel-member. The curtain elements are not necessarily equally dimensioned or formed.

The surface area of the shell-member lip design shall be considered as an additional means for sufficient surface area, as well as a means for additional fixation of the gel-member into the shell-member. The combined surface area of the curtain lip design and the matrix-member design, including any hydrophilic property or grip enhancing feature altogether, form the gel-member bonding to the shell-member and matrix-member rather than to the skin of the patient. As shown in FIG. 9, the ways to design the curtain edge details are virtually unlimited, and may thus be regular or irregular, having sharp corners or round shapes, but shall constitute an overly length of edge-line relative to the projected surface area of the electrode in contact with the skin of the patient.

In the preferred design, the shell-member is obtained by liquid injection molding a silicone component of low durometer, or preform moulding using a high consistency silicone rubber of low durometer. If a durometer of such as 00 shore 50 is used, then the wall thickness of up to 1 mm is acceptable for a limited wall height of approximately 5 mm.

If further details is provided that enhances the flexibility of that wall, such as the curtain design, the wall height can be extended to about 10 mm, or even higher when the added gel compound offer the sufficient flexibility. The flexural stiffness of the overall electrode unit including the gel compound and the lead member shall remain low, allowing the electrode unit to adapt maximally to the structures it is intended to be applied to.

When the durometer of the silicone material for the shell-member is increased, then the dimensional thickness shall be reduced, and wall height ratio shall be increased similarly, to maintain the overall flexibility of the complete electrode unit design. The higher the durometer of the silicone material, the thinner wall thicknesses in general are required to be, in combination with higher wall-height and the flexural properties of the gel-material/s included.

More specifically, the internal structure of the shell-member includes a matrix-member consisting of e.g. distribution of pins or cavity elements, fibres or an open cell sponge. The purpose of this matrix-member is to provide support of the rubbery gel-member, especially important for thicker gel-components, where wall height of above 5 mm is utilized. In combination with ultra-soft gel-material the design of the matrix-member is of further importance, as the matrix-member additionally provides means for integrity protection of the gel-member or its compound materials. The matrix-member supports the rubbery gel-member and allow a high viscosity preferable thixotropic gel-member be arranged within the matrix-member. The properties of the viscous gel compound shall be matched to the density of the matrix-member design, additionally to the layer thickness of the gel-member. If the gel-member is almost aqueous the matrix-member design should be of higher density, than in designs where the gel-member is plasticized to become rubbery during a curing process. An example of a useful gel compound is such as according to the patent U.S. Pat. No. 7,252,792 B2 to Axelgaard, which is commercially available. As the water content may impact the tack-properties of the gel compound, a composite structure of layers of specific formulations is advantageous. Utilizing a thixotropic electrolyte solution, non-plasticized high viscosity gel or low plasticized gel, suspended in the electrode matrix-member, and lidding this material with a sheet of plasticized rubbery gel, results for thicker electrode designs in further soft electrode units. Such a multi-component gel-member design leads to low internal stresses in the gel-member itself during use, providing the intended high-level adaption to the tissue. The properties of the skin layer rubbery plasticized gel compound shall have enough integrity to not disintegrate and leave gross remnants of gel on the skin.

An important feature of the matrix-member is to provide enough surface area to make the gel-member stick to the shell-member when the electrode is detached from the skin. Designing the matrix-member details to have hydrophilic properties further enhances the grip to the gel-member. The integrity of the gel-member is supported by the matrix-member design as the gel-member is cured into the matrix-member and adding only limited rigidity to the final electrode unit. Therefore, the properties of the matrix-member shall allow a high degree of flexibility together with the gel-member, so that the matrix-member does not constitute a stiffness enhancing element.

In proper designed conventional electrodes, care is taken to not have the conductive element getting into contact with the skin. Since the conductive member is often consisting of metal mesh fabrics, skin contact leads to charge concentrations or hot spots, which can be an irritant or even become unsafe. For the shell electrode unit design, this is of limited concern, as no rigid member exist, and thus hot spots are only relevant for dried out electrodes, which would be the case for any hydrogel-based electrode design. To limit any risk related, the matrix-member design should not cause any adverse reactions.

However, it is not intended that the matrix-member come into contact with the skin. This is additionally to secure the largest possible surface area of the gel-member to the skin. In designs where overfilling the shell-member with gel material is part of the intended design, the height of the matrix-member should level that of the wall height maximising integrity protection of the softer gel component.

The matrix-member especially serves to provide sufficient grip for the gel-member to remain within the shell-member, rather than the gel-member stick to the skin of the patient. This is reached through designing the matrix-member to have sufficient surface area and include hydrophilic properties of the matrix-member for application of the conductive member. The properties of the conductive member should include good adhesion for the gel-member. The surface area of the shell-member lip design shall be considered as an additional means for sufficient surface area. The combined surface area of the lip design and the matrix-member design, including any hydrophilic property or grip enhancing feature together form the gel-member bonding to the shell-member and matrix-member rather than to the skin of the patient.

A 50% overhead is considered sufficient, more overhead is however beneficial. If the overhead grip of the matrix-member and shell-member relative to the grip of the skin is too low, the likelihood of the electrode unit to disintegrate is considerable, and thus removal of the electrode is compromised, and doffing becomes unacceptable in daily use.

We claim:

1. An electrode specially adapted for providing suitable electrical contact and fixation to the patient's skin in regions with irregular tissue structures, the electrode comprising:
   a flexible nonconductive shell-member forming a body structure;
   a flexible matrix-member;
   a conductive member;
   a connective member to connect to an external pulse generator;
   a rubbery gel-member;
   wherein the flexible matrix-member is arranged in the shell-member and fixates the conductive member and supports the rubbery gel-member, the conductive member evenly distributing electrical connection from the connective member to the rubbery gel-member, and the rubbery gel-member provides mechanical fixation of the electrode to the patient's skin, wherein the electrode is configured to electrically stimulate at least one of a left branch of a dorsal genital nerve, a right branch of a dorsal genital nerve, and a pudendal nerve of the patient.

2. The electrode according to claim 1, wherein a second conductive gel-member is arranged between the shell-member and the rubbery gel-member.

3. The electrode according to claim 1, wherein the matrix-member comprises a second conductive member being one or more of a graphene or graphitized coating, silver-based coating, or a conductive sponge or conductive fabric mesh member.

4. The electrode according to claim 1, wherein the shell-member comprises natural- or artificial-rubber of a durometer less than or equal to A shore 50.

5. The electrode according to claim 1, wherein the matrix-member is arranged and is constituting a physical structure to enforce the rubbery gel-member and hold the rubbery gel-member into its intended position, while providing structure for the connecting member to form electrical contact to the conductive member, the shell-member is configured to protect the matrix-member and the conductive member from clothing or other parts of the body not intended to be stimulated.

6. The electrode according to claim 1, wherein the matrix-member comprises a plurality of protrusions and cavities, the protrusions forming pins and the cavities forming dimples, the pins and dimples having a first end and a second end, the first end interfacing the shell-member and the second end interfacing the rubbery gel-member.

7. The electrode according to claim 6, wherein the matrix-member is positioned in the shell-member by integrally forming the matrix-member with the shell-member, and wherein the pins and dimples are distributed over the footage of the shell-member and protrude out from or are formed into the shell-member in a straight or angled direction.

8. The electrode according to claim 6, wherein the pins and dimples are an integral part of the shell-member.

9. The electrode according to claim 1, wherein a low friction coating is provided to at least a part of an outer surface of the shell-member.

10. The electrode according to claim 1, wherein the rubbery gel-member comprises a first volume of a gel-member which is thixotropic non-plasticized with high viscosity and a second volume of the gel-member which is plasticized to form a rubbery structure, wherein the first and second volumes form an electrically conductive gel-member providing electrical connection to the patient's skin.

11. The electrode according to claim 1, wherein the connective-member comprises multiple conductive strands.

12. The electrode according to claim 11, wherein the multiple conductive strands are distributed in a fan shaped manner and positioned within the matrix-member or internally in the shell-member above the matrix-member.

13. The electrode according to claim 1, wherein the non-conductive shell-member comprises a structural support for the connective member, in the form of moulded details forming a cavity or a partially covering scrim layer of limited extent.

14. The electrode according to claim 1, wherein the rubbery gel-member comprises a first volume that is non-plasticized and comprises a thickener being one or more of ethylene copolymer or gelatin.

15. The electrode according to claim 14, wherein a density of the matrix-member matches a viscosity of the first volume of the rubbery gel-member, so that the matrix-member and the rubbery gel-member secure electrical contact to the conductive member and the first volume of the rubbery gel-member stays interlocked in the matrix-member.

16. The electrode according to claim 1, wherein the shell-member comprises a wall defining an edge line, and the edge line forms a curtain-like meandering shape adding an expansion spring feature to that edge line.

17. The electrode according to claim 1, wherein the shape of the shell-member is one of a droplet, rectangular, square, circular or oval or multisided.

18. The electrode according to claim 1, further comprising a second rubbery gel-member, and wherein the flexible matrix-member is one of a conductive open cell sponge, a conductive fabric, or conductively coated moulded structures of tailored density forming adhesion support for the second rubbery gel-member.

19. The electrode according to claim 1, further comprising a first liquid-like gel-element and a second rubbery gel-element, wherein the shell-member comprises a low durometer coating that interfaces with the conductive member such that the low durometer coating and the conductive member are configured to evenly distribute the electrical charge in the electrode and provide an electrical connection to the connective member arranged with the flexible matrix-member, the matrix-member providing fixation of the first liquid-like gel-element filled into the matrix member, to a level where the matrix-member provides mechanical support for the second rubbery gel-element converted from a sheet of pre-cured hydrogel, which forms a barrier of the liquid gel-element and forming contact to the patients skin.

* * * * *